(12) United States Patent
Zong et al.

(10) Patent No.: US 8,389,276 B2
(45) Date of Patent: Mar. 5, 2013

(54) IMMORTALIZED MOUSE FIBROBLAST CELL LINES DEFICIENT IN BAX AND/OR BAK

(75) Inventors: Wei-Xing Zong, Philadelphia, PA (US); Craig B. Thompson, Merion, PA (US); Tullia Lindsten, Merion, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1125 days.

(21) Appl. No.: 10/291,549

(22) Filed: Nov. 12, 2002

(65) Prior Publication Data

US 2003/0091982 A1 May 15, 2003

Related U.S. Application Data

(60) Provisional application No. 60/345,085, filed on Nov. 9, 2001.

(51) Int. Cl.
*C12N 5/00* (2006.01)
*C12N 5/02* (2006.01)
*C12N 5/07* (2010.01)
*C12N 5/09* (2010.01)

(52) U.S. Cl. ............ 435/325; 435/440; 435/455; 435/4; 435/354

(58) Field of Classification Search .................. 435/325, 435/6, 7.21, 7.23, 404
See application file for complete search history.

(56) References Cited

U.S. PATENT DOCUMENTS 4,722,888 A * 2/1988 Broder et al. ..................... 435/5
6,245,885 B1 6/2001 Shore et al.

OTHER PUBLICATIONS

Mandic et al, Cisplatin Induces the Proapoptotic Conformation of Bak in a DMEKK1-Dependent Manner, Molecular and Cellular Biology, Jun. 2001, vol. 21, No. 11, pp. 3684-3691.*
Grimes et al, The Gfi-1 protooncoprotein represses Bax expression and inhibits T-cell death Proceedings of the National Academy of Science, Dec. 1996, vol. 93, pp. 14569-14573.*
Rokhlin et al, Fas-mediated Apoptosis in Human Prostatic Carcinoma Cell Lines, Cancer Research, May 1997, vol. 57, pp. 1758-1768.*
Eguchi etg al, Different expression patterns of Bcl-2 family genes in breast cancer by estrogen receptor status with special reference to pro-apoptotic Bak gene, Cell Death and Differentiation, 2000, vol. 7 pp. 439-446.*
Lindsten, T., et al., *The Combined Functions of Proapoptotic Bcl-2 Family Members Bak and Bax Are Essential for Normal Development of Multiple Tissues*, Mol Cell 6:1389-99 (2000).
Wei, M.C., et al., *Proapoptotic Bax and Bak: a Requisite Gateway to Mitochondrial Dysfunction and Death*, Science 292:727-30 (2001).
Zong, W.X., et al., *BH3-only Proteins That Bind Pro-survival Bcl-2 Family Members Fail to Induce Apoptosis in the Absence of Bax and Bak*, Genes Dev 15:1481-6 (2001).
Todaro, G.J., and Green, H., *High Frequency of Sv40 Transformation of Mouse Cell Line 3T3*, Virology 28:756-9 (1966).

* cited by examiner

*Primary Examiner* — Maria Marvich
(74) *Attorney, Agent, or Firm* — Pepper Hamilton LLP

(57) ABSTRACT

The present invention relates to a composition comprising an immortalized cell line which is deficient in the expression of one or more gene(s) of the intrinsic apoptotic pathway, selected from the group consisting of Bax, Bak, and mixtures thereof. The present invention further relates to the product of a process for producing an immortalized mouse fibroblast cell line which is deficient in the expression of Bax, Bak, and mixtures thereof. Finally, the present invention relates to a method and a kit for identifying a compound or composition which induces or blocks the extrinsic apoptotic pathway.

8 Claims, 4 Drawing Sheets

A

B

A

B

IMMORTALIZED MOUSE FIBROBLAST CELL LINES DEFICIENT IN BAX AND/OR BAK

This application claims the benefit of U.S. Provisional Patent Application No. 60/345,085, filed Nov. 9, 2001, the contents of which is hereby incorporated by reference in its entirety.

BACKGROUND OF THE INVENTION

1. Field of Invention

The present invention relates to a composition comprising an immortalized cell line which is deficient in the expression of one or more gene(s) of the intrinsic apoptotic pathway. In particular, said cell line is on deposit and publicly available through the Center for Technology Transfer of the University of Pennsylvania, said cell line having docket number O-2707. The present invention further relates to the product of a process for producing an immortalized mouse fibroblast cell line which is deficient in the expression of one or more of Bax, Bak, or Bax and Bak gene(s). Finally, the present invention relates to a method and a kit for identifying a compound or composition which induces or blocks the extrinsic apoptotic pathway.

2. Background

Programmed cell death, known as apoptosis, is a process where a cell kills itself in response to extrinsic signals, or intrinsic or developmental cues. Organisms use apoptosis to eliminate damaged or unwanted cells. Apoptosis plays a critical role in development and tissue homeostasis. In humans and other mammals, excessive apoptosis may lead to tissue degenerative diseases such as Alzheimer's disease, while insufficient apoptosis leads to uncontrolled cell growth that may result in cancer. Two major apoptotic pathways have been identified: an extrinsic cell death pathway in which apoptosis is initiated through ligand binding to cell surface receptors expressed on the cell that will subsequently die, and an intrinsic cell death pathway in which apoptosis is initiated within the cell.

Tumor necrosis factor receptor family members are among the best characterized of receptors involved in the extrinsic death pathway. Upon the engagement of ligand, these receptors initiate the formation of a death-inducing signaling complex, which includes an essential adaptor molecule FADD. FADD in turn recruits Caspase 8, which in turn is activated through an autoproteolytic process. Once activated, Caspase 8 initiates both the activation of additional caspases such as Caspase 9 and Caspase 3, and the degradation of intracellular substrates, which eventually results in cell death. The TNF receptor family includes TNFR1; Fas; DR3 proteins such as Apo3, WSL-1, TRAMP, and LARD; DR4; DR5 proteins such as TRAIL-R2, TRICK2, and KILLER; and DR6.

Members of the Bcl-2 family of proteins are characterized by their ability to modulate cell death. Bcl-2 and some of its homologues, such as Bcl-xl, inhibit apoptosis, whereas other family members, such as Bax and Bak, induce or accelerate apoptosis under certain conditions. Bak and Bax, as well as Bcl-xs, Bid, and Bik, constitute the pro-apoptotic group of Bcl-2 proteins.

The Bax protein shares highly conserved domains with Bcl-2, some of which are required for the formation of Bax/Bcl-2 heterodimers, which are thought to be important for the survival or death response to apoptotic signals.

Bax expression is elevated in certain tissues after apoptotic stimuli and can be directly regulated by p53. Bax can form ion-conducting channels in lipid bilayers, such as mitochondrial membranes, which may be the biochemical mechanism through which it exerts some of its effects.

Bax was first identified as a protein that co-immunoprecipitated with Bcl-2. Determination of the amino acid sequence of the Bax protein showed it to be highly homologous to Bcl-2. The bax gene encodes a 21 kDa protein which is 96% homologous between mouse and human.

Bak also promotes cell death and counteracts the protection from apoptosis provided by Bcl-2. Like Bax, the Bak gene product primarily enhances apoptotic cell death following an appropriate stimulus. Bak is a potent inducer of apoptosis in various cell types. The predicted mouse Bak protein is 77% identical and 89% similar to its human counterpart.

U.S. Pat. No. 6,245,885, issued Jun. 12, 2001 to Shore, et al., discloses purified polypeptide fragments of the ART domain and the transmembrane domain of the BAX protein which, when administered to a cell, increase or decrease apoptosis of the cell. Also disclosed are methods for identifying compounds which, when administered to a cell, increase or decrease apoptosis of the cell. Also disclosed are methods for diagnosing a patient having, or predisposed to develop, a disease involving altered apoptosis by identifying a mutation in a BAX-encoding gene which results in an amino acid mutation in the BAX ART domain, a BAX transmembrane domain, or that alters the interaction of the BAX ART domain with the BAX transmembrane domain.

To study how the apoptotic machinery is regulated, mice deficient in both Bax and Bak have been produced. In line with the importance of Bax and Bak in apoptosis, such mice show developmental defects in multiple tissues. However, because of the difficulty in breeding Bax/Bak double deficient mice, and the inability of primary cells to proliferate infinitely, the use of primary lymphocytes or fibroblasts to study molecular events of apoptosis is limited.

To satisfy this need in the art, Applicants have developed the inventive immortal mouse embryo fibroblast cell lines, which are Bax/Bak double deficient, Bax deficient, and Bak deficient. Such deficient cell lines are resistant to wide variety of intrinsic death stimuli. The establishment of the inventive immortal cell line provides an unlimited source of Bax and/or Bak deficient cells. The inventive cells are more homogeneous and stable than primary cells. They do not generally change their growth properties during further culturing and propagation, and they have a defined genetic background. They are easy to transfect: unlike primary fibroblasts, where expression vectors can only be transduced through retroviral infection, the inventive immortal cells can be transfected using various standard methods.

The availability of the inventive immortal cell lines will make possible the study of the molecular events of apoptosis which could not previously be studied directly, such as the mechanisms by which these proteins regulate the cell fate of death or survival and how the activities of these proteins are regulated by different survival or death-inducing signals. Further, the inventive cell lines and methods for using the same will make it possible to investigate whether a drug is toxic to cells or protects cells from dying in a mechanism-based manner, as well as to identify and evaluate non-apoptotic side effects.

SUMMARY OF THE INVENTION

The present invention relates to a composition comprising:
a cell of an immortalized cell line which is deficient in the expression of one or more gene(s) selected from the group consisting of Bax, Bak, and mixtures thereof.

The present invention additionally relates to a process for producing an isolated immortalized mouse fibroblast cell line which is deficient in the expression of one or more of Bax, Bak, or Bax and Bak gene(s), which comprises the steps of:

(i) isolating a suspension of Bax, Bak, or Bax and Bak deficient murine embryonic fibroblasts; and (ii) modifying said murine embryonic fibroblasts by repeatedly culturing said cells, wherein said culturing step is repeated until the cells are selected for immortality.

The present invention further relates to a process for producing an immortalized mouse fibroblast cell line which is deficient in the expression of one or more of Bax, Bak, or Bax and Bak gene(s), which comprises the steps of:

(i) isolating a suspension of Bax, Bak, or Bax and Bak deficient murine embryonic fibroblasts;

(ii) modifying said murine embryonic fibroblasts by transfecting said cells in a culture medium containing one or more oncogene(s); and (iii) culturing said fibroblasts in said viral culture medium until the cells reach the immortal stage.

The present invention further relates to a method for identifying a compound or composition which induces or blocks the extrinsic apoptotic pathway, which comprises:

reacting, culturing, or contacting a cell of a cell line which is deficient in the expression of one or more gene(s) selected from the group consisting of Bax, Bak, and mixtures thereof with said compound or composition; and determining or measuring the response to said compound or composition on said cell.

The present invention also relates to a diagnostic kit for identifying a compound or composition which induces or blocks the extrinsic apoptotic pathway, comprising:

a cell of a cell line which is deficient in the expression of one or more gene(s) selected from the group consisting of Bax, Bak, and mixtures thereof; and reagent (s) for determining a response to said compound or composition.

DETAILED DESCRIPTION OF THE INVENTION

Definitions

The term "deficient" as used herein refers to a cell which does not express the mRNA of a gene, a protein product of a gene, or both.

The term "immortalized" as used herein refers to the process of transforming a cell line from one having a finite life span to one having an infinite life span.

The term "oncogene-containing virus" as used herein refers to a class of viruses which express one or more immortalizing gene(s) upon infecting a cell. Exemplary oncogene-containing viruses capable of expressing immortalizing genes include simian virus 40 large T antigen, papillomaviruses E6 and E7, adenovirus E1A, Epstein-Barr virus, human T-cell leukemia virus, herpesvirus saimiri, oncogenes, and mutant p53 gene. A more complete catalogue of oncogene-containing viruses is known to artisans of ordinary skill in the art.

The term "SV40" as used herein refers to simian virus 40 large T antigen.

The term "direct DNA introduction" as used herein refers to a process of introducing exogenous DNA into a target cell. Exemplary methods for direct DNA introduction include, for example and without limitation, calcium phosphate co-precipitation, electroporation, lipofection, and microinjection. Other methods for direct DNA introduction are known to artisans of ordinary skill in the art.

Compositions of the Present Invention

Programmed cell death, known as apoptosis, is a process where a cell kills itself in response to extrinsic signals, or intrinsic or developmental cues. Organisms use apoptosis to eliminate damaged or unwanted cells. Apoptosis plays a critical role in development and tissue homeostasis. In humans and other mammals, excessive apoptosis may lead to tissue degenerative diseases such as Alzheimer's disease, while insufficient apoptosis leads to uncontrolled cell growth that may result in cancer. Two major apoptotic pathways have been identified: an extrinsic cell death pathway in which apoptosis is initiated through ligand binding to cell surface receptors expressed on the cell that will subsequently die, and an intrinsic cell death pathway in which apoptosis is initiated within the cell.

Figure 1:
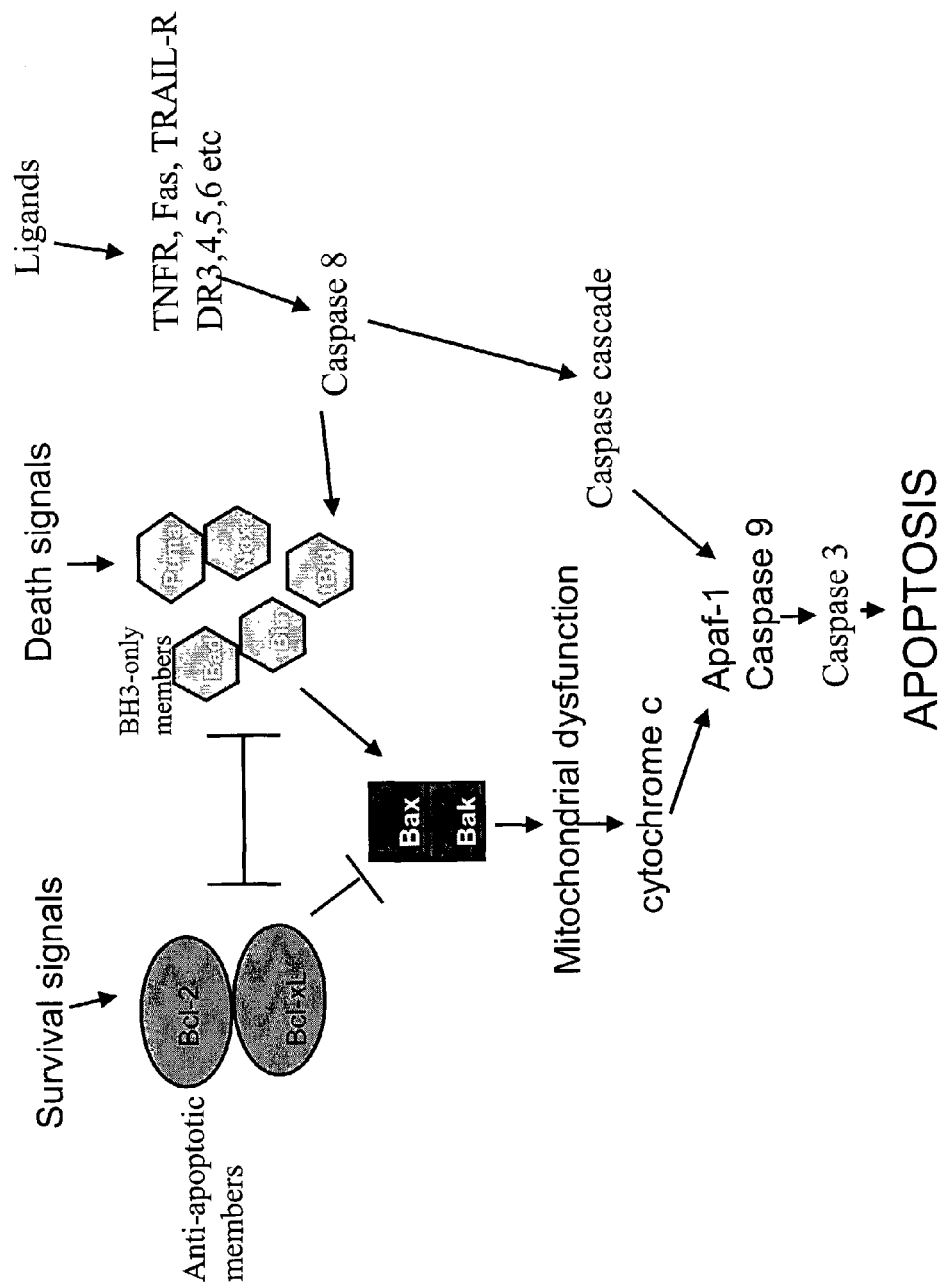
FIG. 1 is a drawing which depicts an overview of the intrinsic and extrinsic apoptosis pathways.

As shown in FIG. 1, the commonly understood cellular intrinsic apoptosis pathway involves several Bcl-2 family proteins. Bax and Bak are the proapoptotic members of this family. They reside in the cytosol or on mitochondria and are kept in an inactive form in normal cells. When a cell is committed to apoptosis, Bax and Bak undergo conformational changes leading to oligomerization and insertion into the mitochondria outer membrane. This process leads to cytochrome c release from mitochondria into the cytosol. Cytochrome c then binds to Apaf-1 and Caspase 9, resulting in the activation of Caspase 9, the subsequent activation of Caspase 3, and ultimately cell death. In some cell types, the extrinsic and intrinsic pathways merge at a point where the BH3-only protein Bid is cleaved and activated by Caspase 8. The truncated form of Bid, tBid, then blocks the anti-apoptotic activity of Bcl-2/Bcl-xL and/or activates the proapoptotic function of Bax/Bak.

The proapoptotic activity of Bax and Bak is regulated by two other groups of proteins in the Bcl-2 family: anti-apoptotic members such as Bcl-2 and Bcl-xL, and pro-apoptotic BH3-only members such as Bid, Bim, Bad, Noxa, Puma, and Bmf. These two groups of proteins antagonize each other and function to either block or activate the pro-apoptotic activity of Bax and Bak, depending on whether the cell is instructed to survive or to die. FIG. 1 schematically depicts the relationship among the Bcl-2 family proteins and the shows the critical importance of Bax and Bak to the intrinsic apoptosis pathway.

To study how the apoptotic machinery is regulated, mice deficient in both Bax and Bak have been produced. In line with the importance of Bax and Bak in apoptosis, such mice show developmental defects in multiple tissues. Unexpectedly, we have found that thymocytes isolated from the Bax/Bak double deficient mice are resistant to cell death induced by λ-irradiation, etoposide, and neglect. Unexpectedly, we have also found that primary fibroblasts isolated from these animals are resistant to UV-irradiation, serum deprivation, chemotherapeutic agents etoposide, staurosporine, as well as ER stress stimuli tharpsigargin, tunicamycin, and brefeldin A. Thus, we have unexpectedly found that deleting Bax and Bak proapoptotic proteins from cells completely mutes the intrinsic cell death pathway. We have also unexpectedly found that these cells remain sensitive to Fas-mediated and TNFR-mediated cell death. The characteristics of Bax/Bak double deficient mice are described in greater detail in our publications: Lindsten, T., Ross, A. J., King, A., Zong, W. X., Rathmell, J. C., Shiels, H. A., Ulrich, E., Waymire, K. G., Mahar, P., Frauwirth, K., Chen, Y., Wei, M., Eng, V. M., Adelman, D. M., Simon, M. C., Ma, A., Golden, J. A., Evan, G., Korsmeyer, S. J., MacGregor, G. R., and Thompson, C. B., *the Combined Functions of Proapoptotic Bcl-2 Family Members Bak and Bax Are Essential for Normal Development of Multiple Tissues*, Mol Cell 6:1389-99 (2000), and Wei, M. C., Zong, W. X., Cheng, E. H., Lindsten, T., Panoutsakopoulou, V., Ross, A. J., Roth, K. A., MacGregor, G. R., Thompson, C. B., and Korsmeyer, S. J., *Proapoptotic Bax and Bak: a Requisite Gateway to Mitochondrial Dysfunction and Death*, Science 292:727-30 (2001), each of which is incorporated by reference in its entirety.

However, because of the difficulty in breeding Bax/Bak double deficient mice, and the inability of primary cells to proliferate infinitely, the use of primary lymphocytes or fibroblasts to study molecular events of apoptosis has heretofore been limited. To satisfy this need in the art, Applicants have developed the inventive immortal mouse embryo fibroblast cell lines, which are Bax/Bak double deficient, Bax deficient, and Bak deficient. Such deficient cell lines are resistant to wide variety of intrinsic death stimuli. Thus, the present invention relates to a composition comprising:

a cell of an immortalized cell line which is deficient in the expression of one or more gene(s) selected from the group consisting of Bax, Bak, and mixtures thereof.

In a preferred embodiment, said cell is deficient in the expression of the Bak gene.

In another preferred embodiment, said cell is deficient in the expression of the Bax gene.

In a more preferred embodiment, said cell is deficient in the expression of both the Bax gene and the Bak gene.

In another preferred embodiment, said composition additionally comprises a medium capable of sustaining growth and replication of the cell.

In a particularly preferred embodiment, said cell is of an immortalized cell line which is deficient in the expression of the Bax and Bak genes, and which is deposited as of Jul. 23, 2008, and publicly available through the American Type Culture Collection ("ATCC"), 10801 University Boulevard, Manassas, Va. 20110, said cell line having accession number PTA-9386.

The establishment of the inventive immortal cell lines provides an unlimited source of Bax and/or Bak deficient cells. The inventive cells are more homogeneous and stable than primary cells. They do not generally change their growth properties during further culturing and propagation, and they have a defined genetic background. They are easy to transfect: unlike primary fibroblasts, where expression vectors can only be transduced through retroviral infection, the inventive immortal cells can be transfected using various standard methods.

The molecular events of apoptosis. We expect that, based on the critical roles of Bcl-2 family proteins in apoptosis, it is extremely important to study the mechanisms by which these proteins regulate the cell fate of death or survival. Our previous work has unexpectedly shown that the deficiency of Bax and Bak results in resistance to a wide range of apoptotic stimuli, as discussed above. Moreover, although the proapoptotic BH3-proteins are able to interact and inactivate the anti-apoptotic Bcl-2 proteins, they are not able to induce death of the Bax/Bak doubly deficient cells. These findings indicate that Bax and Bak are the essential gateway to mitochondrial dysfunction required for cell death. The inventive cell lines, lacking both Bax and Bak or one of them, provide tools to study the function of anti-apoptotic Bcl-2 family proteins, BH3-only proteins, and Bax and Bak proteins themselves. Further, the regulation of the activities of these proteins by different survival or death-inducing signals can now be studied using these cells.

Death receptor-dependent and caspase-dependent cell death. Although the intrinsic mitochondria-dependent cell death pathway is completely blocked by the lack of Bax/Bak, the death receptor-dependent and caspase-dependent death pathways appear to be intact in the inventive Bax/Bak doubly deficient cells. We expect that the ability to completely block the intrinsic death pathway conferred by the availability of the inventive cells will greatly simplify or eliminate the complication of cross-talk between the intrinsic and the extrinsic pathways. Thus, other cell death pathways that are independent of mitochondrial dysfunction can be studied without this complication. Molecules or agents that can induce or block the death receptor-dependent cell death pathway or the caspase-dependent cell death pathway can now be screened and studied in a more defined manner.

Processes of the Present Invention

The present invention relates to a process for producing an isolated immortalized mouse fibroblast cell line which is deficient in the expression of one or more of Bax, Bak, or Bax and Bak gene(s), which comprises the steps of:

(i) isolating a suspension of Bax, Bak, or Bax and Bak deficient murine embryonic fibroblasts; and (ii) modifying said murine embryonic fibroblasts by repeatedly culturing said cells, wherein said culturing step is repeated until the cells are selected for immortality.

In a preferred embodiment, said culturing step is repeated about thirty times.

The present invention further relates to a process for producing an immortalized mouse fibroblast cell line which is deficient in the expression of one or more of Bax, Bak, or Bax and Bak gene(s), which comprises the steps of:

(i) isolating a suspension of Bax, Bak, or Bax and Bak deficient murine embryonic fibroblasts;

(ii) modifying said murine embryonic fibroblasts by transfecting said cells in a culture medium containing one or more oncogene(s); and (iii) culturing said fibroblasts in said viral culture medium until the cells reach the immortal stage.

In a preferred embodiment, said culture medium contains one or more oncogene-containing virus(es).

In a more preferred embodiment, said oncogene-containing virus contains an SV40 large T antigen oncogene.

In another preferred embodiment, said step of transfecting said cells is by direct DNA introduction.

The products and intermediates may be isolated or purified using one or more standard purification techniques known to one of ordinary skill in the art, including, for example, one or more of simple solvent evaporation, recrystallization, distillation, sublimation, filtration, polymerase chain reaction, Southern blotting, Northern blotting, Western blotting, chromatography, including thin-layer chromatography, affinity chromatography, gel filtration chromatography, ion exchange chromatography, FPLC, HPLC (e.g. reverse phase HPLC), column chromatography, flash chromatography, radial chromatography, trituration, salt precipitation, two-phase separation, polymer precipitation, heat denaturation, isoelectric separation, dialysis, and the like.

Methods of the Present Invention

The present invention relates to a method for identifying a compound or composition which induces or blocks the extrinsic apoptotic pathway, which comprises:

reacting, culturing, or contacting a cell of a cell line which is deficient in the expression of one or more gene(s) selected from the group consisting of Bax, Bak, and mixtures thereof with said compound or composition; and determining or measuring the response to said compound or composition on said cell.

Drug screening. As discussed above, the inventive Bax/Bak doubly deficient cells lack a functional mitochondria-dependent cell death machinery, but the caspase-mediated cell death pathway remains intact. Using the inventive cells, assays can now be developed to investigate whether certain drugs are toxic to cells or protect cells from dying in a mechanism-based manner.

The inventive cells are also useful in methods for analyzing the side effects of certain drug candidates on cells. Many compounds, such as etoposide, staurosporin, and brefeldin A, work through an apoptosis-inducing activity, effectively masking other effects, such as toxicity, which may exist. It has been difficult or impossible to study these other effects when a cell is already undergoing apoptosis. We expect that since the intrinsic apoptotic pathway is completely blocked in the inventive Bax/Bak deficient cells, apoptosis-based drug candidates can be applied to the inventive cells, and non-apoptotic effects can be identified and analyzed.

Kits of the Present Invention

The present invention relates to a diagnostic kit for identifying a compound or composition which induces or blocks the extrinsic apoptotic pathway, comprising:

a cell of a cell line which is deficient in the expression of one or more gene(s) selected from the group consisting of Bax, Bak, and mixtures thereof; and reagent(s) for determining a response to said compound or composition.

EXAMPLES

The following examples are illustrative of the present invention and are not intended to be limitations thereon. Unless otherwise indicated, all percentages are based upon 100% by weight of the final composition.

Example 1

Preparation of Immortalized Bax/Bak Doubly Deficient Fibroblasts

Because of the difficulty in breeding Bax/Bak double deficient mice, and inability of primary cells to proliferate infinitely, the use of primary lymphocytes or fibroblasts to study molecular events of apoptosis is limited. We have therefore established an immortal mouse embryo fibroblast cell line which is Bax/Bak double deficient. The following example illustrates the preparation of immortalized Bax/Bak doubly deficient fibroblasts provided according to the present invention.

A. Preparation of murine embryonic fibroblasts. Murine embryonic fibroblasts, hereinafter "MEF", were prepared by the following method. Individual embryos (day 17) were removed from the uterus and tested for Bax and Bak deficiency. MEF were isolated from embryos identified as Bax/Bak doubly deficient. After internal organs, head, and limbs were removed, embryos were cut into small pieces and treated with 5 ml 0.05% Trypsin-EDTA at 4° C. overnight. Trypsin solution was aspirated off and the tube containing the embryo pieces was incubated at 37° C. for 30 minutes. Embryo tissues were then suspended in 5 ml tissue culture medium supplemented with 10% fetal bovine serum, 100 units/ml of penicillin and 100 ug/ml of streptomycin, and pipetted vigorously to break up the tissue. The tissue suspension was allowed to stand for 2 minutes to let the tissue clumps fall and the supernatant containing the individual cells was collected. Cells were spun down and plated in one 10 cm dishes per embryo. 3 days later, when confluent, cells were frozen down using standard procedure and kept at −140° C. until further use.

B. Generation of immortal Bax/Bak doubly deficient fibroblasts. About $2 \times 10^5$ MEF were plated in a 60 mm petri dish in 4 ml of culture medium, and cultured at 37° C., 5% $CO_2$ until they were confluent. Cells were washed with 3 ml phosphate buffered saline, and were trypsinized with 0.5 ml trypsin-EDTA for 5 minutes at room temperature. One ml of medium was added to resuspend the cells. Cell numbers were counted using a hematocytometer. 0.5 ml of the total 1.5 ml cell suspension was transfer into 3.5 ml fresh medium for a 1:3 split and continuous culturing. This process is considered one passage, and was repeated until the cells reach the immortal stage in about 30 passages.

Figure 2:
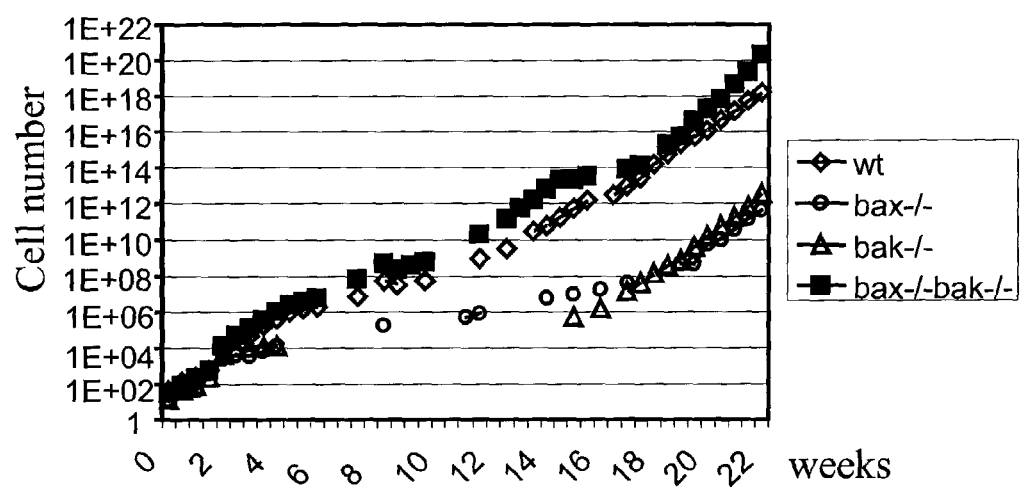
FIG. 2A is a graph which depicts the number of cells in culture during establishment of the immortal cell lines that are deficient in Bax, Bak, or both, which reached a stage of stable growth in 16-18 weeks.
FIG. 2B is a photograph of an SDS-PAGE Western Blot gel that depicts protein expression of Bax and Bak in four immortalized cell lines.
Figure 2:
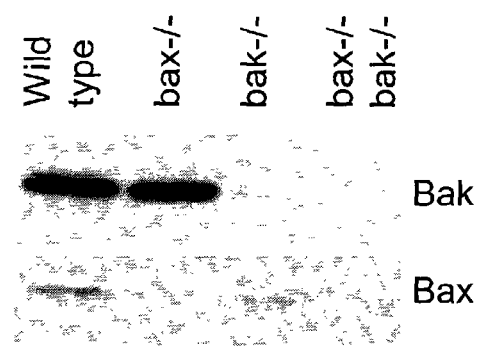

Embryo fibroblasts from wild type, bax-/-, bak-/-, or bax-/-bak-/-mice were cultured in DMEM medium supplemented with 10% FBS and 1% pen/strep. Cells were diluted and passed when confluent. As shown in FIG. 2A, after about 16-week culturing, equivalent to about 30 passages, the Bax/Bak doubly deficient cells reach a stably proliferating state with a doubling time of about 24 hours. Immortalized cell lines with different genotypes were lysed and 20 µg of total protein were separated on SDS-PAGE. Polyclonal antibodies against Bax or Bak were used to detect protein expression. The lack of expression of Bax and Bak in these cell lines was confirmed by Western Blotting, as shown in FIG. 2B.

Example 2

Preparation of Immortalized Bax/Bak Doubly Deficient Fibroblasts

A. Preparation of murine embryonic fibroblasts. Murine embryonic fibroblasts were prepared as in Example 1.

B. Generation of immortal Bax/Bak doubly deficient fibroblasts. Immortalized Bax/Bak doubly deficient fibroblasts were generated using the 3T3 protocol (See, e.g., Todaro, G. J., and Green, H. *High frequency of SV40 transformation of mouse cell line 3T3*, Virology 28:756-9 (1966)). About 2×10⁵ nondividing MEF cells uniformly in phase G-1 of the cell cycle were plated in a 60 mm petri dish in 4.0 ml of culture medium containing SV40 large T antigen DNA, and were cultured in 0.5 ml of the virus preparation at 37° C., 5% $CO_2$ until they were confluent. Cells were washed with 3.0 ml phosphate buffered saline (PBS), and were trypsinized with 0.5 ml trypsin-EDTA for 5 minutes at room temperature. The cells were then centrifuged and resuspended in 1.0 ml of the virus medium. Cell numbers were counted using a hematocytometer. 0.5 ml of the total 1.5 ml cell suspension was transferred into each of three fresh petri dishes with 3.5 ml fresh medium for a 1:3 split. This process is considered one passage, and was repeated until the cells reach the immortal stage in about 30 passages.

Example 3

Preparation of Immortalized Bax or Bak Singly Deficient Fibroblasts

Using the procedure described in Example 1, immortal cell lines of MEF isolated from wild type, Bax singly deficient, and Bak singly deficient mouse embryos were established. As described above, the lack of expression of Bax or Bak in the latter two cell lines was confirmed by Western Blotting, as shown in FIG. 2B.

Example 4

Immortalized Bax/Bak Doubly Deficient Cells Resist Intrinsic Death Signals

Figure 3:
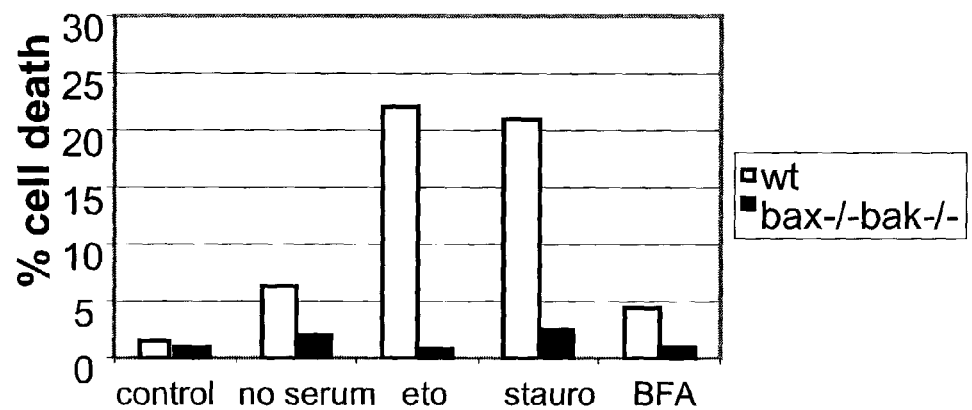
FIG. 3A is a graph which depicts the percentage death rate of wild type and Bax/Bak doubly deficient immortalized cells treated with serum deprivation, etoposide, staurosporin, or brefeldin A.
FIG. 3B is a graph which depicts the percentage death rate of wild type and Bax/Bak doubly deficient immortalized cells infected with a retrovirus that expresses Puma, Bad, or Bim proteins.
Figure 3:
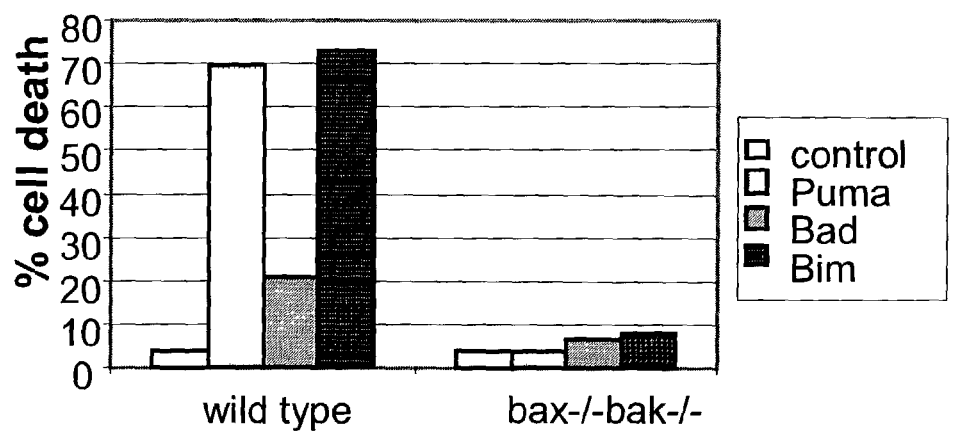

This example relates to determining that immortalized Bax/Bak doubly deficient cells are resistant to wide variety of death stimuli, including BH-3 only proapoptotic proteins. To test whether immortal Bax/Bak double deficient cells behave like primary Bax/Bak double deficient cells in resisting intrinsic cell death stimuli, wild type and Bax/Bak doubly deficient cells were treated with serum deprivation, etoposide (100 μM), staurosporin (4 μM), or brefeldin A (10 μg/ml). 24 hours later, cells were stained with DAPI (1 μg/ml), and death rate determined by FACS. Wild type immortal cells were killed by each of these death stimuli. On the other hand, Bax/Bak doubly deficient cells survived these death stimuli, as shown in FIG. 3A. This is consistent with the findings in the primary MEF cells.

In addition, cells were infected with retrovirus that express Puma, Bad, or Bim, together with GFP. 24 hours later, cells were stained with DAPI and subjected to FACS analysis. Percentage of cell death was determined by the ratio of DAPI positive dead cells and GFP positive cells. As shown in FIG. 3B, Bax/Bak doubly deficient cells were resistant to the expression of each of the proapoptotic BH3-only proteins Bim, Bad, and Puma, whereas wild type cells were killed by the expression of these proteins.

Example 5

Immortalized Bax/Bak Doubly Deficient Cells Remain Sensitive to Caspase-dependent Apoptosis This example relates to determining that immortalized Bax/Bak doubly deficient cells remain sensitive to caspase-dependent apoptosis. Upon activation, Bax and Bak undergo conformational change and oligomerize on the mitochondria outer membrane, and induce the release of cytochrome c from mitochondria into cytosol. Cytochrome c binds to Apaf-1 and caspase 9, which results in the activation and auto-cleavage of caspase 9, which in turn activate downstream caspases such as caspase 3.

Figure 4:
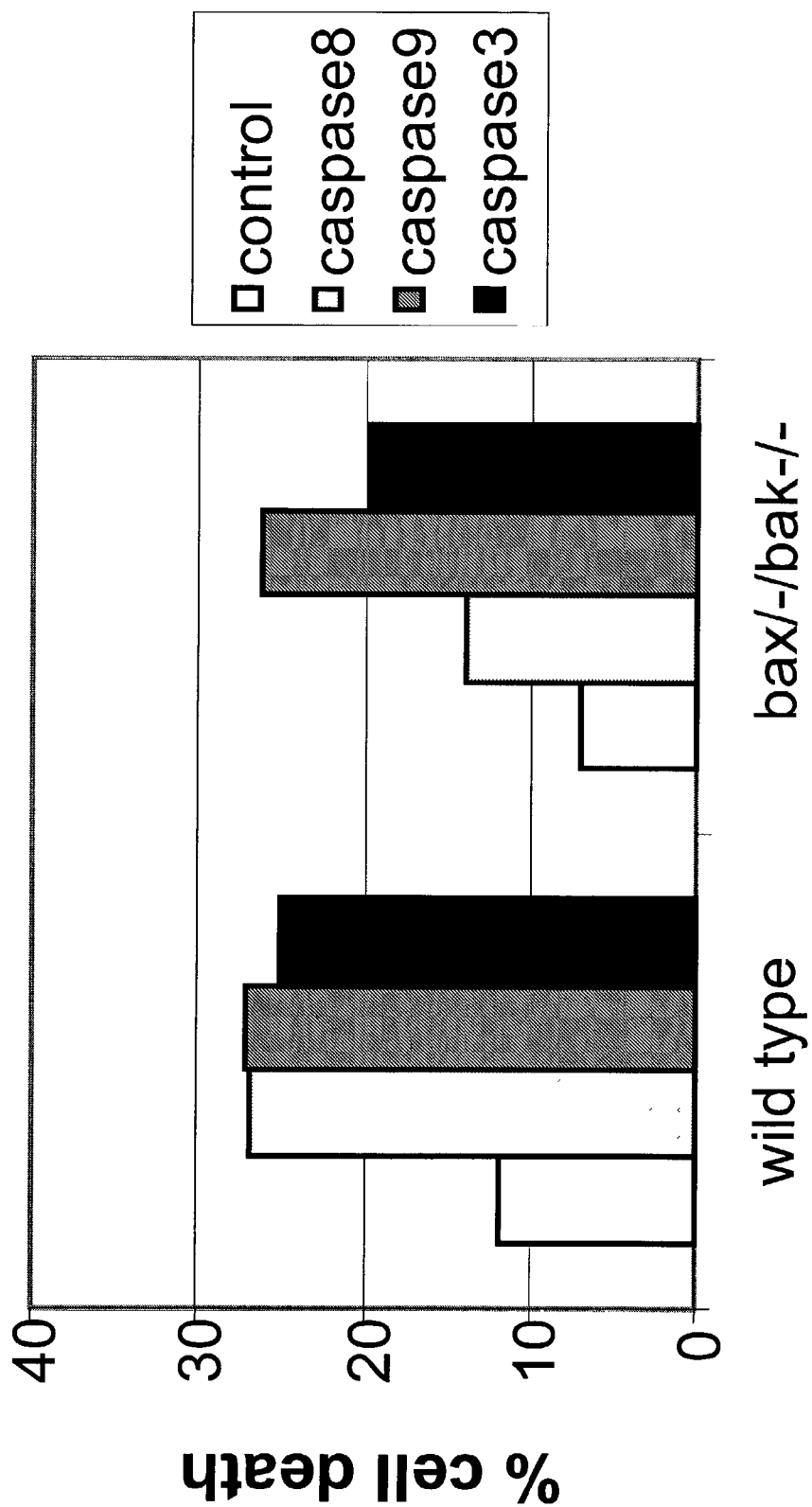
FIG. 4 is a graph which depicts the percentage death rate of wild type and Bax/Bak doubly deficient immortalized cells transfected with a vector that expresses caspase 8, caspase 9, or caspase 3.

Although the apoptosis machinery is interrupted at the Bax/Bak level in the doubly deficient cells, the cell death pathway components were expected to still be intact downstream of Bax/Bak. To test this, wild type and Bax/Bak doubly deficient immortal cell lines were transfected with vectors expressing caspase 8, caspase 9, or caspase 3, together with GFP expressing vector. 24 hr later, the cells were stained with 1 μg/ml DAPI for 10 min, and subjected to FACS analysis. Cell death rate was determined by the number of DAPI positive dead cells over GFP positive cells. As shown in FIG. 4, both caspase 9 and caspase 3 killed wild type and doubly deficient cells essentially equally well, indicating that the downstream apoptosis machinery is intact and functional in Bax/Bak deficient cells.

The invention being thus described, it will be obvious that the same may be modified or varied in many ways. Such modifications and variations are not to be regarded as a departure from the spirit and scope of the invention and all such modifications and variations are intended to be included within the scope of the following claims.

We claim:

1. A composition comprising a cell of an immortalized cell line which does not express Bak mRNA and Bak protein.

2. The composition of claim 1, wherein said cell does not express Bax mRNA and Bax protein.

3. The composition of claim 1, additionally comprising a medium capable of sustaining growth and replication of the cell.

4. A composition comprising a cell of an immortalized cell line wherein said cell line is identified as having ATCC accession number PTA-9386.

5. A diagnostic kit for identifying a compound or composition which induces or blocks an extrinsic apoptotic pathway of a cell, comprising a cell of a cell line that does not express Bak mRNA and Bak protein.

6. The diagnostic kit of claim 5, wherein said cell does not express Bax mRNA and Bax protein.

7. The diagnostic kit of claim 5, additionally comprising a medium capable of sustaining growth and replication of the cell.

8. A diagnostic kit for identifying a compound or composition which induces or blocks an extrinsic apoptotic pathway of a cell, comprising a cell of a cell line wherein said cell line is identified as having ATCC accession number PTA-9386.

* * * * *